United States Patent
Birnkrant et al.

(10) Patent No.: US 7,563,010 B2
(45) Date of Patent: Jul. 21, 2009

(54) ENDOSCOPIC LIGHT SOURCE SAFETY AND CONTROL SYSTEM WITH OPTICAL SENSOR

(75) Inventors: Dashiell Birnkrant, Worcester, MA (US); Vernon Hopkins, Worcester, MA (US); Dana J. Landry, Sturbridge, MA (US)

(73) Assignee: Karl Storz Endovision, Inc., Charlton, MA (US)

( * ) Notice: Subject to any disclaimer, the term of this patent is extended or adjusted under 35 U.S.C. 154(b) by 468 days.

(21) Appl. No.: 11/245,512

(22) Filed: Oct. 7, 2005

(65) Prior Publication Data

US 2007/0083085 A1    Apr. 12, 2007

(51) Int. Cl.
    *A61B 1/06* (2006.01)
(52) U.S. Cl. .............. 362/574; 362/231; 362/804; 600/178; 600/181
(58) Field of Classification Search ........... 362/572, 362/574, 575, 231, 804; 600/160, 178, 179–182
    See application file for complete search history.

(56) References Cited

U.S. PATENT DOCUMENTS

| 4,356,534 | A |   | 10/1982 | Hattori |
|---|---|---|---|---|
| 4,433,675 | A | * | 2/1984 | Konoshima ............ 600/178 |
| 4,580,557 | A | * | 4/1986 | Hertzmann ............ 606/12 |
| 4,963,960 | A |   | 10/1990 | Takami |
| 5,172,685 | A | * | 12/1992 | Nudelman ............ 600/108 |
| 5,850,496 | A |   | 12/1998 | Bellahsene et al. |
| 6,110,107 | A |   | 8/2000 | Bellahsene et al. |
| 6,689,050 | B1 |   | 2/2004 | Beutter et al. |
| 6,932,809 | B2 | * | 8/2005 | Sinofsky ............ 606/12 |
| 6,944,204 | B2 | * | 9/2005 | Zhou et al. ............ 372/109 |
| 6,949,069 | B2 | * | 9/2005 | Farkas et al. ............ 600/178 |
| 7,160,014 | B2 | * | 1/2007 | Sasaki et al. ............ 362/574 |
| 2004/0064019 | A1 |   | 4/2004 | Chang et al. |
| 2005/0023356 | A1 | * | 2/2005 | Wiklof et al. ......... 235/462.42 |
| 2005/0036755 | A1 |   | 2/2005 | Horne |
| 2006/0184037 | A1 | * | 8/2006 | Ince et al. ............ 600/476 |

FOREIGN PATENT DOCUMENTS

JP    2001-321338    11/2001

* cited by examiner

*Primary Examiner*—Stephen F. Husar
*Assistant Examiner*—Peggy A. Neils
(74) *Attorney, Agent, or Firm*—St. Onge Steward Johnston & Reens LLC (57) ABSTRACT

Disclosed is an endoscope light source safety system including visible light transmitted along an illumination path; a source for providing radiation along at least a portion of the illumination path; an illumination attenuator connectable to the illumination path for receiving said visible light and the radiation; a first reflector connected to said illumination attenuator for reflecting at least a portion of the radiation received by said illumination attenuator; a combiner for combining the radiation from said source into the illumination path; and a detector for receiving at least a portion of the radiation reflected from said first reflector and for generating a signal indicative of the receipt of visible light by said illumination attenuator.

34 Claims, 5 Drawing Sheets

ENDOSCOPIC LIGHT SOURCE SAFETY AND CONTROL SYSTEM WITH OPTICAL SENSOR

FIELD OF THE INVENTION

The invention relates to endoscopic systems, and more specifically to an endoscopic system having an optical detection means for determining the presence of an endoscope.

BACKGROUND OF THE INVENTION

Conventional endoscopes are often supplied with illumination from an external light source. Such light sources generally include high powered lamps, such as xenon lamps. The light sources are generally coupled to the endoscope by means of a detachable waveguide or fiber optic light cable.

An endoscope may be disconnected from the waveguide while still energized by the light source. Light exiting from the waveguide may therefore cause damage if the waveguide is set down without the medical instrument attached. For example, the light may damage operating drapes, a patient's skin, or clothing. Therefore, it is desirable that the light exiting the waveguide be attenuated when the endoscope is determined to be disconnected from the waveguide.

Some devices exist to determine the presence of a light cable on a light source. For example, U.S. Pat. No. 4,356,534 to Hattori discloses a light supply device having a means for detecting a connection between a connector of a cable and a light supply socket using a relay switch operated by a solenoid. U.S. Pat. No. 4,433,675 to Konoshima discloses a light supply apparatus for an endoscope having a detecting section to detect the state of a coupling between a connector and a socket mounted on a housing of the light supply. However, Both Hattori and Konoshima disclose only means for detecting the presence of a connection between a connector and a socket of a light supply. Neither patent discloses a system for detecting the presence of an endoscope on a waveguide.

U.S. Pat. No. 6,110,107 to Bellahsene et al. discloses a fiber optic cable for supplying light to an endoscope and for detecting the presence of the endoscope. However, the specialized cable disclosed in Bellahsene requires electrical conductors running the length of the cable and a switch on the cable's end with a sensor configured to sense the proximity of the endoscope. Therefore, the teachings of Bellahsene may not be used to detect the presence of an endoscope in existing endoscopic systems without using the specialized cable.

It is therefore desired to provide an improved system and method for detecting the presence of an illumination attenuator, such as an endoscope, along an illumination path. It is a further desired to provide such a system that is adaptable to existing illumination attenuator systems without the necessity for a specialized cable or waveguide.

SUMMARY OF THE INVENTION

According, it is an object of the present invention to provide an endoscopic system having an optical detection means for determining the presence of an endoscope or any other illumination attenuator. It is a further object to provide the endoscopic system in which the system controls a light source providing illumination to the illumination attenuator.

It is a further object of the present invention to provide an optical sensor for detecting the presence of an endoscope in an endoscopic system. It is a further object to provide the optical sensor is adaptable to existing endoscopic systems.

These and other objectives are achieved by providing an endoscope light source safety system, comprising visible light transmitted along an illumination path; a source for providing radiation along at least a portion of the illumination path; an illumination attenuator connectable to the illumination path for receiving said visible light and the radiation; a first reflector connected to said illumination attenuator for reflecting at least a portion of the radiation received by said illumination attenuator; a combiner for combining the radiation from said source into the illumination path; and a detector for receiving at least a portion of the radiation reflected from said first reflector and for generating a signal indicative of the receipt of visible light by said illumination attenuator.

Further provided is an endoscope light source safety system, comprising visible light transmitted along an illumination path; a source for providing radiation along at least a portion of the illumination path; an illumination attenuator connectable to the illumination path for receiving said visible light and the radiation; a first reflector connected to said illumination attenuator for reflecting at least a portion of the radiation received by said illumination attenuator; an optical element for combining the radiation from said source into the illumination path and diverting the reflected radiation away from the illumination path; and a detector for receiving at least a portion of the radiation reflected from said optical element and for generating a signal indicative of the receipt of visible light by said illumination attenuator.

Further provided is an optical sensor for detecting the presence of an illumination attenuator comprising a source for providing radiation to an illumination path; a detector for receiving reflected radiation from the illumination path, said detector receiving the reflected radiation via a detection path; a sensor reflector for receiving the radiation from the source and transmitting at least a portion of the radiation along the illumination path to an illumination attenuator, receiving the reflected radiation, wherein the reflected radiation is reflected from the illumination attenuator, and transmitting at least a portion of the reflected radiation along the detection path to the detector, wherein a signal indicative of the presence of the illumination attenuator is generated when the detector receives reflected radiation.

DETAILED DESCRIPTION OF THE INVENTION

Figure 1:
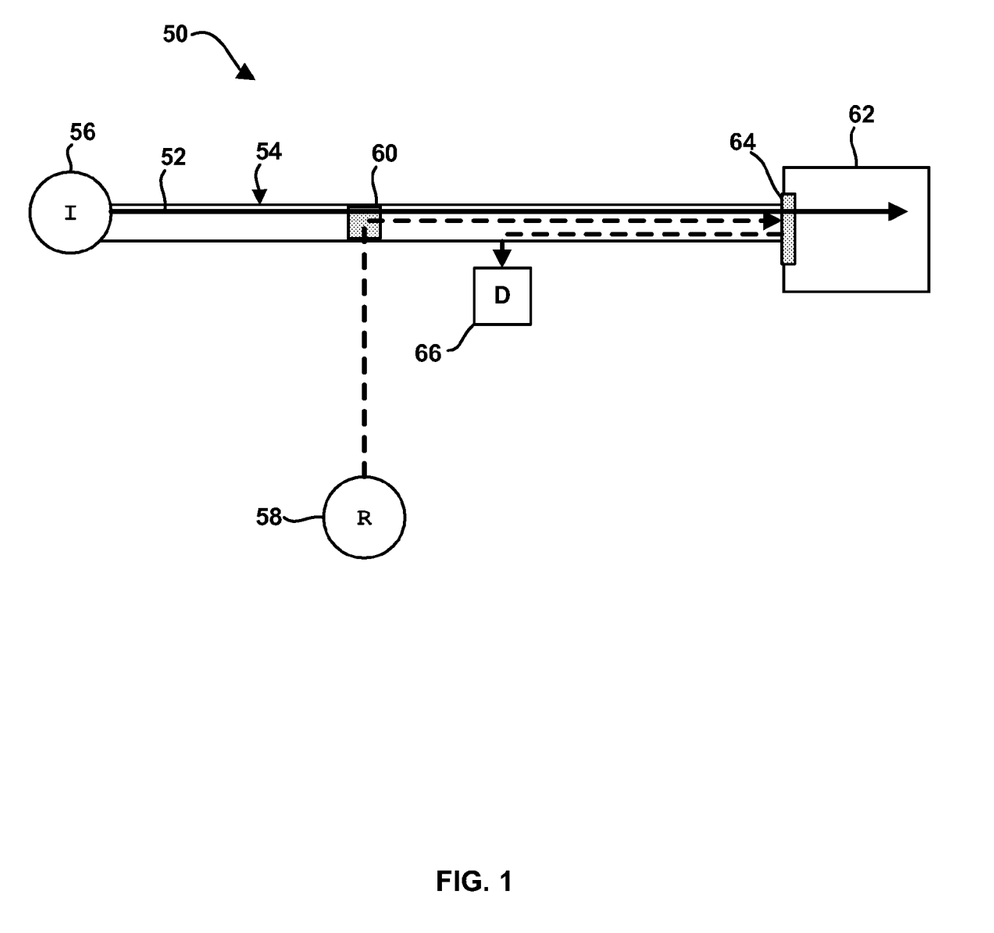
FIG. 1 is a schematic diagram of an endoscopic system according to the present invention.

FIG. 1 shows a schematic of an endoscopic system 50 according to the present invention. The system 50 includes visible light 52 being transmitted along an illumination path 54. In some embodiments, the visible light 52 may originate from an illuminator 56. The system 50 also includes a source 58 for providing radiation along at least a portion of the illumination path 54. The radiation may be combined into the illumination path 54 via a combiner 60.

Further included in the system 50 is an illumination attenuator 62. The illumination attenuator 62 may be any device for receiving visible light. Preferably, the illumination attenuator 62 is a device being capable of also transmitting or projecting a portion of the visible light. For example, the illumination attenuator 62 may be an endoscope or a similar surgical instrument.

The system 50 includes a reflector (e.g., first reflector 64) connected to the illumination attenuator 62 for reflecting at least a portion of the radiation received by the illumination attenuator 62. The first reflector 64 may be mounted within the illumination attenuator 62 or external to the illumination attenuator 62. In some embodiments, the first reflector 64 is in the illumination path 54 and transmits at least a portion of visible light received by the illumination attenuator 62.

A detector 66 is included in the system 50. The detector 66 may receive a portion of radiation reflected from the first reflector 64. The detector 66 may further generate a signal (not shown) indicative of the receipt of visible light 52 by the illumination attenuator 62. In some embodiments, the signal is provided to control the amount of visible light provided by an illuminator (e.g., illuminator 56).

Figure 2:
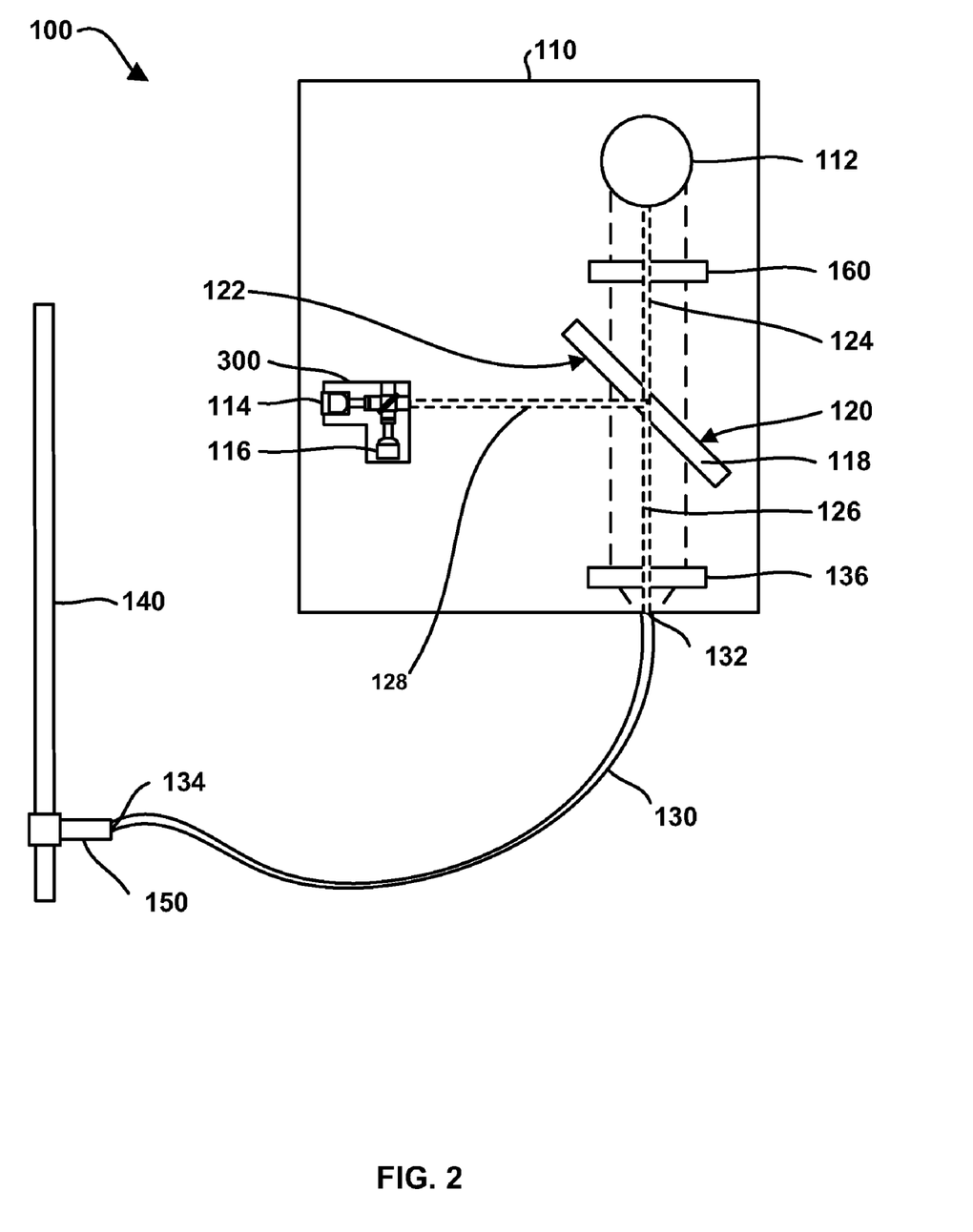
FIG. 2 is a schematic diagram of another endoscopic system according to the present invention.

FIG. 2 shows a schematic of an exemplary embodiment of an endoscopic system 100 according to the present invention. The system 100 includes an illumination supply device 110. The illumination supply device 110 includes an illuminator 112 for providing visible light (e.g., visible light 52). The visible light may be provided at a first frequency or a first frequency range (e.g., within the visible range of the electromagnetic spectrum). The illuminator 112 may be any known illuminator, such as a xenon lamp.

The illumination supply device 110 further includes a source 114 for providing radiation (e.g., detection radiation) at a second frequency or second frequency range. In a preferred embodiment, the second frequency range is less than the first frequency range (e.g., infrared radiation frequencies and visible light frequencies, respectively). For example, the source 114 may be an IR light emitting diode ("LED") providing infrared ("IR") radiation. In other embodiments, the second frequency range may be greater than the first frequency range (e.g., ultraviolet radiation frequencies and visible light frequencies, respectively). The source 114 may provide constant radiation or modulated radiation, i.e., at a particular pulse rate. For example, the source 114 may provide radiation pulsed at 455 kHz with a 4.2 kHz envelope.

The illumination supply device 110 of the endoscopic system 100 further includes a detector 116 (e.g., IR receiving module). The detector 116 may generate a signal upon the receipt or detection of particular radiation or light. For example, the detector 116 may generate a signal upon the receipt of a specific frequencies or levels of radiation being reflected from a reflector and/or illuminator attenuator.

In some embodiments, the detector 116 may generate a signal when radiation pulsed at a particular pulse rate is received. For example, the detector 116 may only detect radiation being pulsed at a rate of 455 kHz within a 1-22.5 kHz envelope. Such limits on detection and signal generation are desirable to prevent interferants from being detected, such as fluorescent light, incandescent lights, sun light or the visible light (e.g., 52). The detector 116 may further include built-in electronics such as a demodulator and/or gain control (not shown).

As shown in FIG. 2, the endoscopic system 100 may include a waveguide 130 detachably connectable to the illumination supply device 110 (e.g., via a waveguide socket (not shown)). The waveguide 130 includes a proximal end 132 and a distal end 134. The waveguide 130 may be any waveguide or light cable for providing an illumination path, such as a fiber optic cable. The endoscopic system 100 further includes an illumination attenuator 140 (e.g., an endoscope) being connectable to the illumination supply device 110 via the waveguide 130. For example, the illuminator attenuator 140 may include a waveguide fitting 150 (e.g., a light post connector) detachably connected to the distal end 134 of the waveguide 130.

Figure 3:
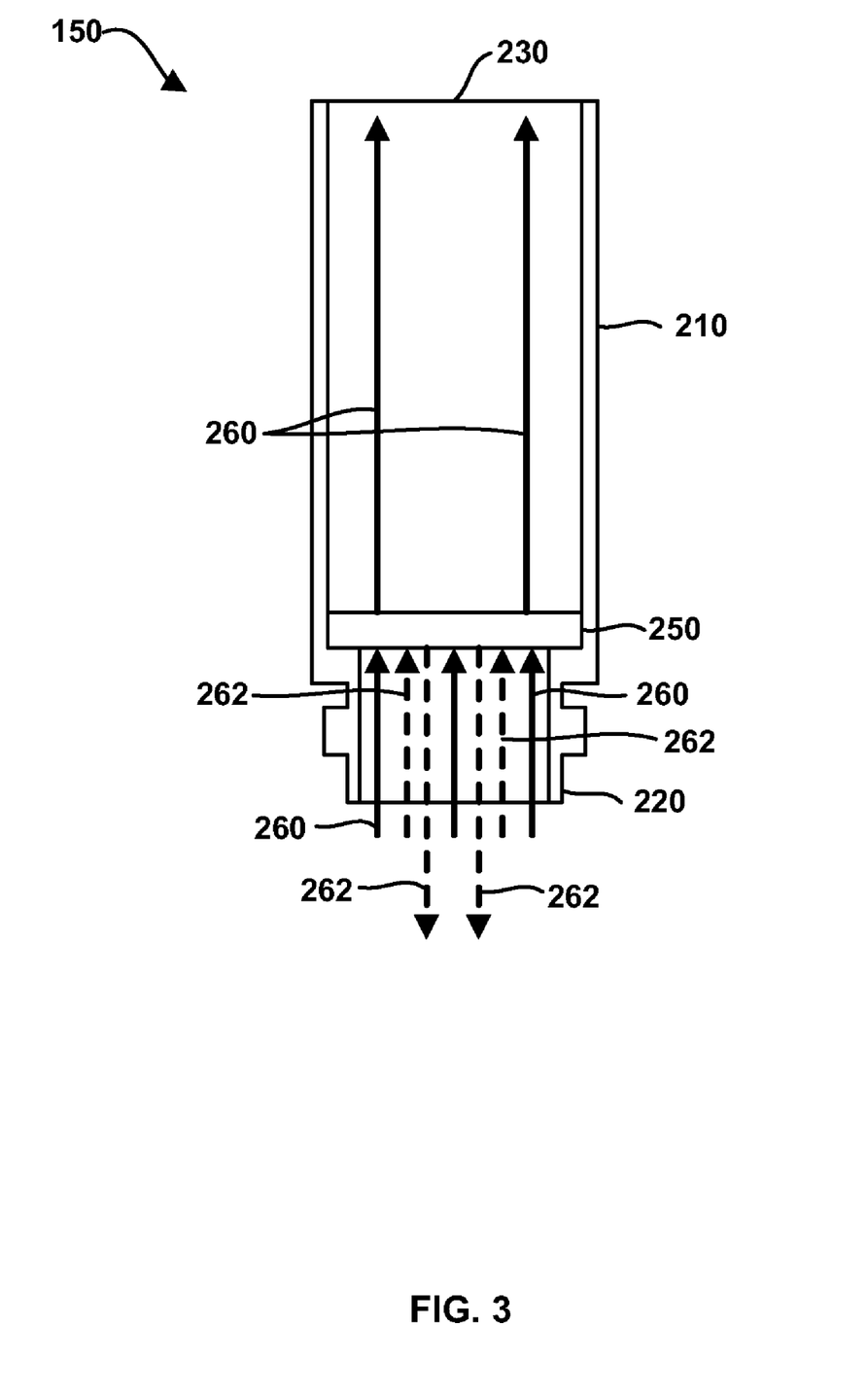
FIG. 3 is a cross sectional view of a waveguide fitting portion of the endoscopic system shown in FIG. 2.

A cross sectional view of the waveguide fitting 150 is shown in FIG. 3. The waveguide fitting 150 includes a housing 210 having a first end 220 and a second end 230. The first end 220 includes a means to detachably connect the waveguide fitting 150 to the waveguide 130. The second end 230 includes a means to detachably connect to the illuminator attenuator 140. In some embodiments, the second end 230 may be disconnected from the illuminator attenuator 140 only after the first end 220 is disconnected from the waveguide 130. Some embodiments of the waveguide fitting 150 may be adaptable to several known illumination attenuators (e.g., endoscopes) and waveguides. Therefore, the present invention may be readily implemented with (e.g., interchangeable between) existing endoscopic instruments, waveguides, and illumination supply devices.

The waveguide fitting 150 includes a first reflector 250. In one embodiment, the first reflector 250 may be, e.g., a "hot mirror" for transmitting the visible light and reflecting other light or radiation (e.g., radiation 260). The first reflector 250 may receive both visible light 260 and radiation 262 from the illumination supply device 110 via the waveguide 130. The first reflector 250 transmits a substantial portion of visible light 260 via the illuminator attenuator 140. The first reflector 250 reflects a substantial portion of radiation 262 to the detector 116 via the waveguide 130. As explained in more detail below, the presence of the illumination attenuator 140 may therefore be determined by detecting (via detector 116) whether radiation is reflected (i.e., an illumination attenuator 140 is attached) or not reflected (i.e., the illumination attenuator 140 is detached).

In other embodiments, the first reflector 250 may include, e.g., a cold filter. As one of ordinary skill in the art will understand, a cold filter may be employed to reflect shorter wavelengths of light or radiation and transmit longer wavelengths. For example, a cold filter may be used when the radiation has a higher frequency than the visible light. In some other embodiments, the first reflector 250 may include a notch filter to reflect one or more narrow bands of radiation or light and transmit wider regions of radiation around the rejected band(s).

The first reflector 250 may further include a unique indicator (not shown). Such indicator may provide information (e.g., parameters) from the illuminator attenuator 140 to the illumination supply device 110 via the reflected radiation 264. The parameters may be stored in the indicator or provided to the indicator by a user via a remote control (not shown) on the illuminator attenuator 140. The parameters may include, for example, an illumination attenuator or endoscope type, serial number, maximum temperature, a maximum light level input, and/or the remote controls present. For example, the indicator may include an integrated circuit providing parameters (e.g., instructions) to the illumination supply device 110, such as to adjust the intensity of the illuminator 112 in real time.

As shown in FIG. 2, the illumination supply device 110 may further include an optical element 118 (e.g., a "hot mirror" and/or a second reflector). The optical element 118 includes a first surface 120 and a second surface 122. The optical element 118 is positioned to receive visible light from the illuminator 112 via the first surface 120, and reflect radiation from (e.g., and to) the source 114 via the second surface 122. For example, the optical element 118 may be positioned at approximately a forty-five degree angle relative to a first portion 124 (from the illuminator 112) and approximately a forty-five degree angle relative to a radiation path 128 (from the source 114). In the exemplary embodiment, the first portion 124 is oriented ninety degrees relative to the radiation path 128.

As one of ordinary skill in the art will understand, the optical element 118 may be implemented in conventional illumination supply devices, in part, by removing a current zero degree mirror and replacing it with the above described forty-five degree hot mirror. The orientation of the optical element 118 in the present invention allows for the rejection of radiation from the lamp (e.g., illuminator 112), but further creates a radiation path for the transmission of radiation to and from the detector 116.

As shown in FIG. 2, the optical element 118 may receive visible light from the illuminator 112 via a first portion 124 of an illumination path and transmit the visible light to the waveguide 130 (i.e., combined into the illumination path) via a second portion 126 (e.g., via a lens 136). The optical element 118 may further receive radiation (from the source 114) via a radiation path 128 and reflect the radiation to the waveguide 130 via the second portion 126. If the illuminator attenuator 140 is present (i.e., connected to the waveguide 130), the radiation, or a substantial portion thereof, will be reflected from the first reflector 250 and returned via the waveguide 130 and second portion 126. The optical element 118 may receive the reflected radiation via the second light 126 path and reflect the radiation to the detector 116 via the radiation path 128 (i.e., diverted from the illumination path).

If the illuminator attenuator 140 is not present, little or no radiation will be returned via the waveguide 130 or received by the detector 116. The illuminator 112 may be controlled (e.g., powered down or turned off) depending on the radiation received. For example, the illuminator 113 may provide visible light only while the detector 116 receives at least a predetermined amount or level of the radiation (e.g., radiation having the second frequency and/or radiation modulated at the particular pulse rate). The illuminator 112 may further not provide visible light when the detector 116 receives less than the predetermined amount of radiation.

Shown in FIG. 2, the illumination supply device 110 may include an iris 160 for controlling the illuminator 112. For example, the iris 160 may block visible light, or any portion thereof, being provided by the illuminator 112. The iris 160 may be positioned along the first portion 124. As one of ordinary skill in the art will understand, such placement of the iris 160 will allow for the control of visible light without interrupting the transmission and/or reflection of the radiation. The iris 160 may (e.g., upon receiving information from the detector 116) block a substantial portion of the visible light when the detector 116 does not receive radiation within a specific frequency range (e.g., a detection frequency range) and/or particular pulse rate (e.g., repetition rate).

Figure 4:
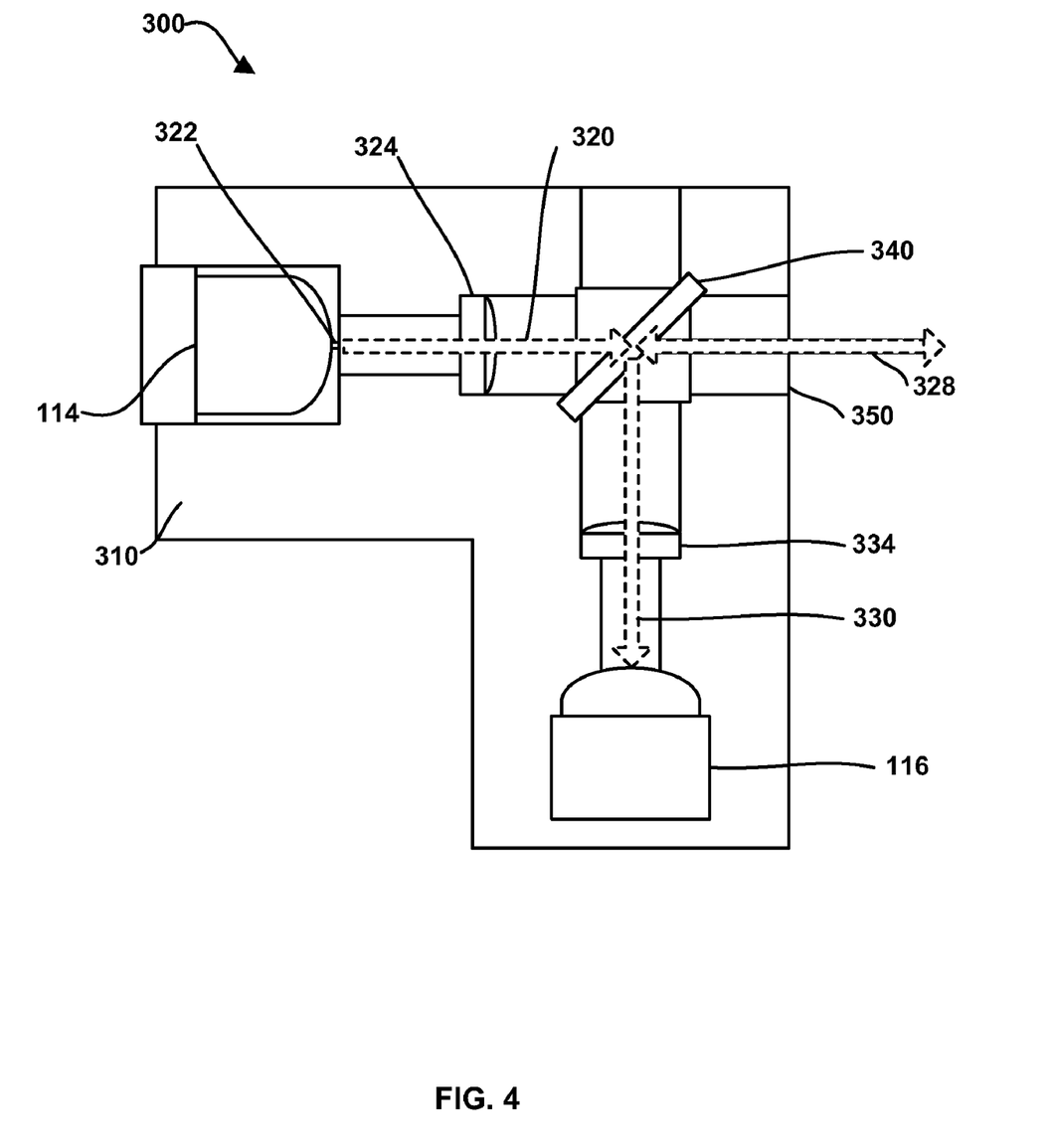
FIG. 4 is a schematic diagram of an optical sensor portion of the endoscopic system shown in FIG. 2.

In one embodiment of the present invention, the source 114 and the detector 116, described above, may be integrated in an optical sensor 300. FIG. 4 shows a schematic diagram of the optical sensor 300 for detecting the presence of an endoscope according to the present invention.

The optical sensor 300 includes a housing 310 and the source 114 (e.g., an infrared radiation source). The source 114 provides radiation along a source path 320. The source 114 may include a field stop 322 (e.g., 0.25 mm pinhole). Further included may be a collimating lens 324 positioned along the source path 320. The optical sensor 300 further includes the detector 116 for receiving reflected radiation via a detection path 330. A focusing lens 334 may be included along the detection path 330.

Shown in FIG. 4, the optical sensor 300 includes a sensor reflector 340. The sensor reflector 340 may be any reflector and/or filter for allowing a portion of received radiation to pass through while reflecting another portion. For example, the sensor reflector 340 may be a 50/50 infrared beam splitter. The sensor reflector 340 receives the radiation (e.g., provided at a specific detection frequency or range of detection frequencies) via the source path 320 and transmits the radiation to the illumination attenuator 140 via an output/return port 350 and the radiation path 328. The sensor reflector 340 may further receive reflected radiation, i.e., reflected from the first reflector 250 of the illumination attenuator 140, via the radiation path 328. The sensor reflector 340 then transmits a portion of reflected radiation to the detector 116 via the detection path 330.

The optical sensor 300 may positively detect the presence of the endoscopic device 140 (i.e., attached to the waveguide 140) when the detector 116 receives reflected radiation within the detection frequency range (and/or a particular pulse rate). The detector 116 may then provide information to the system 100 to adjust or control the illuminator 112 as needed. The optic sensor 300 may detect the presence of the endoscopic device 140 at given time intervals, continuously, and/or upon command by the system 100. The optical sensor 300 is preferably small enough to fit in existing illumination supply devices. For example, one embodiment of the optical sensor 300 may include the following approximate dimensions: 26 mm height, 24 mm width, and 14 mm thickness.

Figure 5:
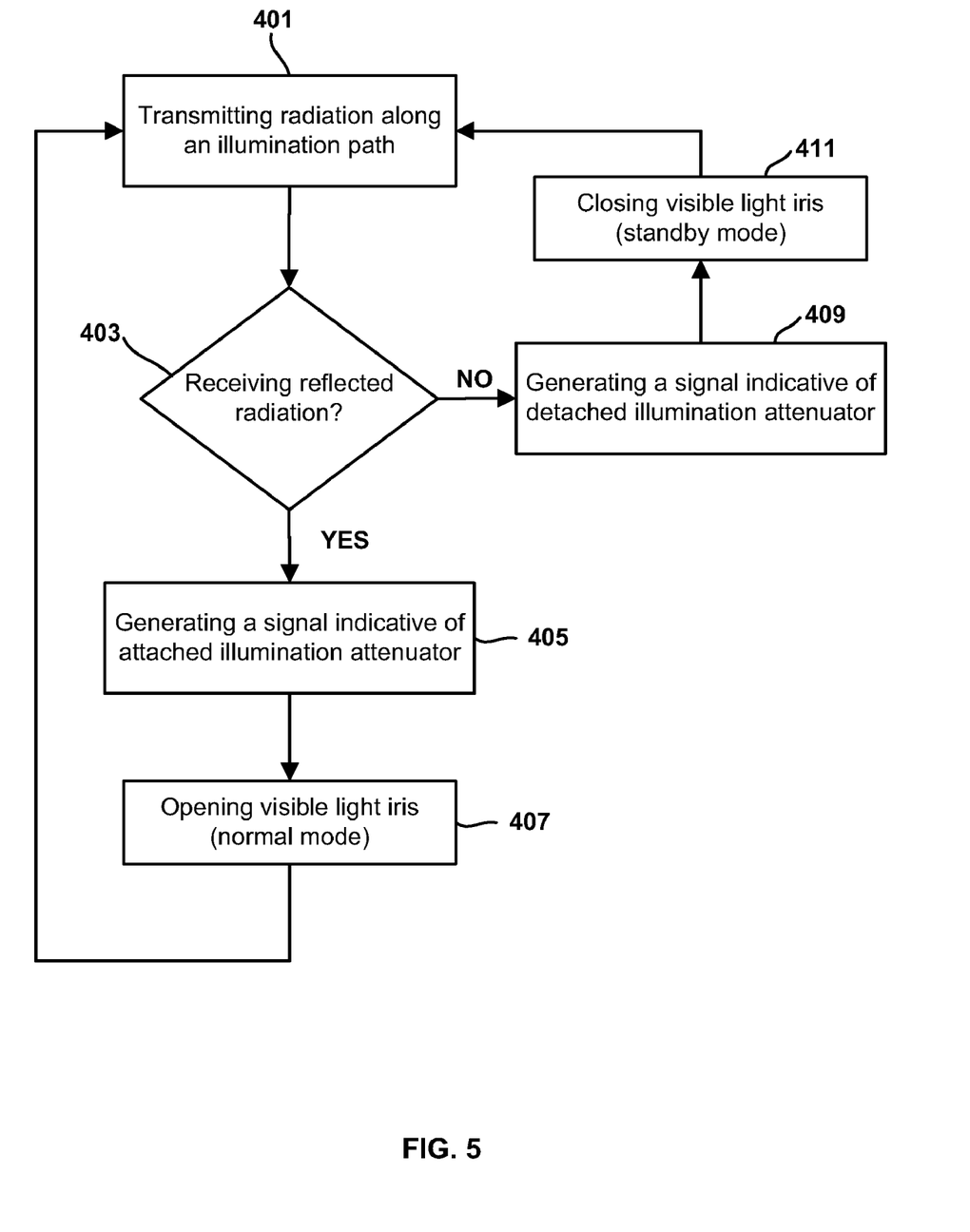
FIG. 5 is a method for controlling an endoscope light source employable by the systems shown in FIG. 1 and FIG. 2.

FIG. 5 shows a method for controlling an endoscope light source according to the present invention. The method is described with respect to the system 100 shown in FIGS. 1-4. However, one of ordinary skill in the art will understand that the method may be implemented in other systems and devices. The method includes a step 401 of transmitting radiation (e.g., a infrared radiation) along an illumination path. The radiation may, e.g., be transmitted at a detection frequency (and/or a pulse rate) to an endoscope via a waveguide. Step 403 includes detecting (e.g., via detector 116) the receipt of reflected radiation from the illumination path, e.g., being reflected from the first reflector 250 via the waveguide 130. If reflected radiation is received (by detector 116), a signal is generated that is indicative of an illumination attenuator being present and/or connected along the illumination path (step 405). The iris 160 may then be opened (or may remain open) allowing the illuminator 112 to transmit visible light (step 407). If the radiation is not received, a signal is generated that is indicative of an illumination attenuator not being present and/or being detached from the waveguide (step 409). The iris 160 may then be closed (or may remain closed) preventing the illuminator 112 from transmitting visible light (step 411).

Advantages of the present invention include the provision of a system and method for accurately detecting the presence of an illuminator attenuator using radiation. Furthermore, the present invention provides a system and method to in which no electrical conductors need be connected to the endoscope to detect its presence. The electronics of the detection system may be contained within the illumination supply device and therefore no custom waveguide is required.

A further advantage of the present invention is the provision of an optical detection system by which parameters of an endoscope or information may be provided to the illumination supply device via radiation.

A further advantage of the present invention is the provision of the system and method being adaptable to existing endoscopic systems and components. It is contemplated that the present invention may be implemented in many existing illumination supply devices.

Although the invention has been described with reference to a particular arrangement of parts, features and the like, these are not intended to exhaust all possible arrangements or features, and indeed many modifications and variations will be ascertainable to those of skill in the art.

What is claimed is:

1. An endoscope light source safety system, comprising:
   visible light transmitted along an illumination path;
   a source for providing radiation along at least a portion of the illumination path;
   a combiner for combining the radiation from said source into the illumination path;
   an illumination attenuator connectable to the illumination path for receiving said visible light and the radiation;
   a first reflector connected to said illumination attenuator for reflecting at least a portion of the radiation received by said illumination attenuator and transmitting at least a portion of said visible light via said illumination attenuator; and
   a detector for receiving at least a portion of the radiation reflected from said first reflector and for generating a signal indicative of the receipt of visible light by said illumination attenuator.

2. The endoscope light source safety system according to claim 1, further comprising:
   an illuminator for transmitting said visible light, wherein the signal is provided for controlling said illuminator.

3. The endoscope light source safety system according to claim 1, wherein the radiation is provided at a pulse rate.

4. The endoscope light source safety system according to claim 3, wherein said detector generates the signal upon receipt of radiation having the pulse rate.

5. The endoscopic system according to claim 3, further comprising:
   an iris positioned in the illumination path for blocking at least a portion of the visible light.

6. The endoscopic system according to claim 5, wherein said iris blocks at least a portion of the visible light when the detector does not receive radiation having the pulse rate.

7. The endoscope light source safety system according to claim 1, wherein said source and said detector are mounted in a sensor housing.

8. The endoscope light source safety system according to claim 1,
   wherein said first reflector is connected externally to said illumination attenuator.

9. The endoscope light source safety system according to claim 1,
   wherein said first reflector is connected internally to said illumination attenuator.

10. The endoscope light source safety system according to claim 1, wherein the illumination path includes a waveguide.

11. The endoscope light source safety system according to claim 1,
    wherein said illumination attenuator is an endoscope.

12. The endoscopic system according to claim 1, further comprising:
    an indicator connected to said first reflector for providing parameters of the illuminator attenuator via the radiation,
    wherein said detector receives the parameters.

13. An endoscope light source safety system, comprising:
    visible light transmitted along an illumination path;
    a source for providing radiation along at least a portion of the illumination path;
    an illumination attenuator connectable to the illumination path for receiving said visible light and the radiation;
    a first reflector connected to said illumination attenuator and in the illumination path for reflecting at least a portion of the radiation and transmitting at least a portion of said visible light received by said illumination attenuator; and
    a detector for receiving at least a portion of the radiation reflected from said first reflector and for generating a signal indicative of the receipt of visible light by said illumination attenuator.

14. The endoscope light source safety system according to claim 13, further comprising:
    an illuminator for transmitting said visible light, wherein the signal is provided for controlling said illuminator.

15. The endoscope light source safety system according to claim 13, wherein the radiation is provided at a pulse rate.

16. The endoscope light source safety system according to claim 15, wherein said detector generates the signal upon receipt of radiation having the pulse rate.

17. The endoscope light source safety system according to claim 13, wherein said source and said detector are mounted in a sensor housing.

18. An endoscope light source safety system, comprising:
    visible light transmitted along an illumination path;
    a source for providing radiation along at least a portion of the illumination path;
    an illumination attenuator connectable to the illumination path for receiving said visible light and the radiation;
    a first reflector connected to said illumination attenuator for reflecting at least a portion of the radiation received by said illumination attenuator and transmitting at least a portion of said visible light via said illumination attenuator;
    an optical element for combining the radiation from said source into the illumination path and diverting the reflected radiation away from the illumination path; and
    a detector for receiving at least a portion of the radiation reflected from said optical element and for generating a signal indicative of the receipt of visible light by said illumination attenuator.

19. The endoscope light source safety system according to claim 18, wherein said optical element is a second reflector.

20. The endoscope light source safety system according to claim 18, wherein said optical element is in the illumination path and transmits at least a portion of said visible light along the illumination path.

21. The endoscope light source safety system according to claim 18, wherein said visible light is transmitted at a first frequency range and the radiation is provided at a second frequency range.

22. The endoscope light source safety system according to claim 21, wherein said detector generates the signal upon receipt of radiation at the second frequency range.

23. The endoscopic system according to claim 21, wherein the first frequency range is greater than the second frequency range.

24. The endoscopic system according to claim 21, wherein the first frequency range at least partially falls within the visible spectrum and the second frequency range at least partially falls within the infrared spectrum.

25. The endoscopic system according to claim 21, wherein the second frequency range is greater than the first frequency range.

26. The endoscopic system according to claim 21, further comprising:
an iris positioned in the illumination path for blocking at least a portion of the visible light.

27. The endoscopic system according to claim 26, wherein said iris blocks at least a portion of the visible light when the detector does not receive radiation within the second frequency range.

28. The endoscope light source safety system according to claim 18, wherein the radiation is provided at a pulse rate.

29. The endoscope light source safety system according to claim 28, wherein said detector generates the signal upon receipt of radiation having the pulse rate.

30. An optical sensor for detecting the presence of an illumination attenuator comprising:
a housing including a source path and a detection path;
a source for providing radiation via the source path to an illumination path, wherein the illumination path is external to the housing;
a detector for receiving reflected radiation from the illumination path, said detector receiving the reflected radiation via the detection path;
a sensor reflector in said housing for:
receiving the radiation from the source and transmitting at least a portion of the radiation along the illumination path to an illumination attenuator,
receiving the reflected radiation, wherein the reflected radiation is reflected from the illumination attenuator, and
transmitting at least a portion of the reflected radiation along the detection path to the detector,
wherein a signal indicative of the presence of the illumination attenuator is generated when the detector receives reflected radiation.

31. The optical sensor according to claim 30, wherein the radiation is provided at a pulse rate.

32. The optical sensor according to claim 30, wherein the source includes a light emitting diode ("LED").

33. A method for controlling an endoscope light source, comprising the steps of:
transmitting radiation along an illumination path to a reflector connected to an illumination attenuator;
transmitting visible light along the illumination path;
reflecting at least a portion of the radiation received by the reflector and transmitting at least a portion of the visible light via the reflector to the illumination attenuator;
detecting the receipt of the reflected radiation from the reflector via the illumination path; and
generating a signal indicative of the presence of the illumination attenuator when the reflected radiation is detected.

34. The method for controlling an endoscope light source according to claim 33, further comprising the step of:
generating a signal indicative of the illumination attenuator not being present if the reflected radiation is not detected; and
preventing the visible light from being transmitted along the illumination path if the reflected radiation is not detected.

* * * * *